United States Patent [19]
Luo et al.

[11] Patent Number: 5,989,872
[45] Date of Patent: Nov. 23, 1999

[54] METHODS AND COMPOSITIONS FOR TRANSFERRING DNA SEQUENCE INFORMATION AMONG VECTORS

[75] Inventors: Ying Luo, Los Altos; Shaobing Hua, Cupertino; Li Zhu, Palo Alto, all of Calif.

[73] Assignee: Clontech Laboratories, Inc., Palo Alto, Calif.

[21] Appl. No.: 08/909,525

[22] Filed: Aug. 12, 1997

[51] Int. Cl.$^6$ .......................... C12P 19/34; C12N 15/85; C12N 15/64; C07H 21/04

[52] U.S. Cl. .................... 435/91.2; 435/91.4; 435/91.41; 435/455; 435/463; 435/465; 435/325; 435/354; 435/366; 536/23.1; 536/24.1; 536/24.2; 536/24.33

[58] Field of Search ............................... 435/5, 91.2, 91.4, 435/91.41, 455, 463, 465, 325, 354, 366; 536/23.1, 24.1, 24.2, 24.33

[56] References Cited

PUBLICATIONS

Bendixen, Christian et al., "A Yeast Mating–Selection Scheme for Detection of Protein–Protein Interactions," *Nucleic Acids Research* (1994) vol. 22, No. 9:1778–1779.

Chien, Cheng–Ting et al., "The Two–Hybrid System: A Method to Identify and Clone Genes For Proteins That Interact With A Protein of Interest," *Proc. Natl. Acad. Sci. USA* (1991) vol. 88:9578–9582.

Degryse, Eric et al., "In Vivo Cloniong by Homologous Recombination in Yeast Using a Two–Plasmid–Based System," *Yeast* (1995) vol. 11:629–640.

Fields, Stanley et al., "A Novel Genetic System to Detect Protein–Protein Interactions," *Nature* (1989) vol. 340:245–246.

Gietz, Daniel et al., "Improved Method For High Efficiency Transformation Of Intact Yeast Cells," *Nucleic Acids Research* (1992) vol. 20, No. 6:1425.

Glasunov, A.V. et al., "Different Repair Kinetics For Short and Long DNA Double–Strand Gaps in *Saccharomyces Cerevisiae*," *Int. J. Radiat. Biol.* (1995) vol. 68, No. 4:421–428.

Guarente, Leonard "Strategies For The Identification Of Interacting Proteins", *Proc. Nat. Acad. Sci. USA* (1993) vol. 90:1639–1641.

Ishioka, Chikashi et al., "Screening Patients For Heterozygous p53 Mutations Using A Functional Assay In Yeast," *Nature Genetics* (1993) vol. 5:124–129.

Ishioka, Chikashi et al., "Detection of Heterozygous Truncating Mutations In The BRCA1 and APC Genes By USing A Rapid Screening Assay In Yeast," *Proc. Natl. Acad. Sci. USA* (1997) vol. 94:2449–2453.

Hopkin, Karen "Yeast Two–Hybrid Systems: More Than Bait And Fish," *The journal of Nih Research* (1996) vol. 8:27–29.

Lorenz, Michael et al., "Gene Disruption With PCT Products In *Saccharomyces Cerevisiae*," *Gene* (1995) vol. 158:113–117.

Luo, Ying et al., "Cloning and Analysis of DNA–Binding Proteins by Yeast One–Hybrid and One–Two–Hybrid Systems," *BioTechniques* (1996) vol. 20:564–568.

Botstein, Dr. D., "The Molecular Analysis of Gene Function in the Yeast *S. Cerevisiae* Has Been Aided Tremendously by the Development of Methods for the Manpfulation of," *Gene* (1987) vol. 58:201–216.

Manivasakam, Palaniyandi et al., "Micro–Homology Mediated PCR Targeting in *Saccharomyces Cerevisiae*," *Nucleic Acids Research* (1995) vol. 23, No. 14:2799–2800.

Shinohara, Akira et al., "Homologous Recombination and the Roles of Double–Strand Breaks," *Tibs* (1995) vol. 20:387–391.

Zhu, Li "Yeast GAL4 Two–Hybrid System," *Methods in Molecular Biology* (1997) vol. 63:173–196.

*Primary Examiner*—David Guzo
*Attorney, Agent, or Firm*—Bozicevic, Field & Francis, LLP; Bret Field

[57] ABSTRACT

Methods and compositions are provided for transferring DNA sequence information from a first vector to a second vector. In the subject methods, a first vector comprising a region of DNA having a sequence of interest is contacted with a set of three pairs of oligonucleotide primers under conditions sufficient to produce three different PCR products, where each product corresponds to a different reading frame. The oligonucleotide primers comprise a first region of sequence identity with the first vector and a second region permissive of site specific recombination with the second vector. The resultant PCR products are combined with the second vector under conditions sufficient for site specific recombination to occur. Also provided are kits for use in performing the subject methods.

22 Claims, No Drawings

METHODS AND COMPOSITIONS FOR TRANSFERRING DNA SEQUENCE INFORMATION AMONG VECTORS

INTRODUCTION

1. Technical Field

The field of this invention is molecular biology.

2. Background of the Invention

In many molecular biological applications, one desires to transfer at least the DNA sequence information of a portion of a first vector to a second vector. For example, the cloning and expression of a particular gene typically involves a cloning step in which the gene is present in a first vector, such as a plasmid, and propagated in a bacterial host, such as *E.coli*. For expression, one may then wish to express the gene in a non-bacterial host, such as a yeast or mammalian cell. Accordingly, the sequence information of the gene must then be transferred from the first vector to an expression vector. To accomplish this transfer of sequence information, the DNA encoding the gene is typically excised or physically separated from the first vector and inserted into the second vector.

Techniques of transferring sequence information from one vector to another, such as that described above, are complex and time consuming, as they require extensive DNA in vitro manipulation, including restriction enzyme digestion, ligation, host transformation and the like. Furthermore, there are a plurality of problems which could occur during the process, such as incompatibility of restriction sites between the cloning and expression vector, insertion in a non-reading frame, and the like. As such, while readily performed, current methods of transferring sequence information from one vector to another are by no means perfect. Furthermore, while the transfer of sequence information from one vector to another of a single gene can be complex, the complexity of such a procedure is amplified exponentially when one desires to transfer information from a plurality of first vectors to a plurality of second vectors.

Accordingly, there is continued interest in the development of new methodology for transferring DNA sequence information among vectors. Of particular interest would be the development of methodologies which are particularly suited for efficient transfer of sequence information from a plurality of first vectors to a plurality of second vectors.

Relevant Literature

Sambrook, Fritsch & Maniatis, Molecular Cloning: A Laboratory Manual (Cold Spring Harbor Laboratory Press) (1989) provides a review of vector preparation, cloning and expression.

The two-hybrid assay is described in U.S. Pat. No. 5,580,736, as well as in Bartel et al., Cellular Interactions in Development: A Practical Approach (Oxford University Press)(1993) pp 153–179; Chien et al., Proc. Nat'l. Acad. Sci. USA (1991)88:9578–9582; Fields & Song, Nature (1989) 340:245–247; Fritz & Green, Current Biol. (1992) 2:403–405; and Guarente, Proc. Nat'l. Acad. Sci. USA (1993) 90:1639–1641. A review of the current status of yeast two-hybrid analysis and related assays is provided in Hopkin, J. NIH Res. (1996) 8:27–29.

SUMMARY OF THE INVENTION

Methods and compositions are provided for transferring DNA sequence information among vectors. In the subject methods, a first vector comprising a region of DNA having a sequence of interest is contacted with a set of three pairs of oligonucleotide primers under conditions sufficient to produce three different primer extension products, where each primer extension product corresponds to one of the three potential reading frames of the DNA region. The oligonucleotide primers contain a first region of sequence identity with the first vector and a second region permissive of site specific recombination with the second vector into which introduction of the DNA sequence information of interest is desired, e.g. an expression vector. In the next step of the subject methods, the primer extension or PCR products are contacted with the second vector under conditions sufficient for site specific recombination to occur. Also provided are kits for use in the subject methods. The subject methods find use in a variety of applications, including the preparation of expression vectors for use in two-hybrid assays.

DESCRIPTION OF THE SPECIFIC EMBODIMENTS

Methods and compositions are provided for transferring DNA sequence information from a first vector to a second vector. In the subject methods, an initial vector comprising a region of DNA having a sequence of interest is contacted with a set of three pairs of oligonucleotide primers under conditions sufficient to produce three different primer extension or PCR products, where each product corresponds to a different reading frame of the three possible reading frames of the DNA sequence of interest. Each nucleotide primer comprises a first domain that has sequence identity with the first vector and a second domain that is permissive of site specific recombination with a second vector, such as an expression plasmid. The resultant PCR products are then contacted with the second vector under conditions sufficient for site specific recombination to occur, resulting in production of the second vector comprising the PCR product and effective transfer of the DNA sequence information from the first to the second vector. The subject methods find use in any application where the transfer of DNA sequence information from one vector to another is desired, and are particularly suited for use in applications where the rapid production of a plurality of expression vectors comprising different uncharacterized DNA sequences of interest, e.g different ESTs, is desired, such as two-hybrid analysis assays.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The first step in the subject methods is to contact a first vector comprising a region of DNA having a sequence of interest with a set of three pairs of oligonucleotide primers under conditions sufficient to produce three sets of primer extension or PCR products, where the vector may be phage vector, a plasmid vector, and the like. Where the first vector is a plasmid, the plasmid will typically be from about 2.5 to 10 kbp, usually from about 3 to 8 kbp in length in which the region of DNA of interest is flanked on both the 5' and 3' end of each strand, i.e. on either side, with regions of known sequence. By "region of DNA having a sequence of interest" is meant any DNA molecule having a specific sequence, either known or unknown, of which introduction into a vector is desired. The region of DNA of interest will generally be a region of DNA encoding a gene of interest or fragment thereof, where the gene may be characterized or not, e.g. an EST sequence, where the sequence may be of known or unknown sequence, and in many applications will be unknown, and will range in length from about 15 bp to 10 kbp, usually from about 500 bp to 8 kbp. The first vector plasmid may be a previously known and even commercially available plasmid vector, or a custom made plasmid vector. A variety of plasmid vectors are known and include pBR322, pUC18, pUC19, pSP64, pSP65, pGEM-3Z, pGEM-3Zf−, pGEM-4, pGEM-4Z,πAN13, Bluescript M13+, Bluescript M13−, and the like. Plasmid first vectors comprising the region of DNA of interest include both those that are custom prepared just prior to use, through standard molecular biological techniques known to those of skill in the art, and those that are purchased from commercial sources, such as genomic, cDNA or other libraries which may be sold in vectors, e.g. as sold by Clontech, Invitrogen, Stratagene and the like.

By contacting the first vector with the set of primers is meant that the first vector and the primers are combined into a reaction mixture, which further comprises any additional requisite or desirable PCR reagents. The polymerase chain reaction (PCR), in which nucleic acid primer extension product is enzymatically produced from template DNA, such as the first vectors of the subject invention, is well known in the art, being described in U.S. Pat. Nos.: 4,683,202; 4,683,195; 4,800,159; 4,965,188 and 5,512,462, the disclosures of which are herein incorporated by reference.

Generally, to perform PCR, the various PCR reagents, including dNTPs, polymerases, buffers, primers and the like, are combined into a reaction mixture. In preparing the reaction mixture, the various constituent components may be combined in any convenient order. For example, the buffer may be combined with primer, polymerase and then template DNA, or all of the various constituent components may be combined at the same time to produce the reaction mixture.

Following preparation of the reaction mixture, the reaction mixture is subjected to a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 90 to 100° C., usually from about 92 to 96° C. and more usually from about 94 to 95° C. for a period of time ranging from about 10 sec to 10 mins, usually from about 15 sec to 3 mins.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 30 to 72° C. and usually from about 37 to 68° C. Annealing conditions will be maintained for a period of time ranging from about 15 sec to 5 min, usually from about 15 sec to 2 min.

Following annealing of primer to template DNA, the reaction mixture will be subjected to conditions sufficient to provide for polymerization of dNTPs to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture will typically be raised to a temperature ranging from about 65 to 75° C., usually from about 68 to 72° C. and maintained for a period of time ranging from about 30 sec to 15 min, usually from about 1 min to 10 min.

The above cycles of denaturation, annealing and polymerization may be performed using an automated device, typically known as a thermal cycler. Thermal cyclers that may be employed are described in U.S. Pat. Nos 5,612,473; 5,602,756; 5,538,871; and 5,475,610, the disclosures of which are herein incorporated by reference.

As mentioned above, a set of three different pairs of oligonucleotide primer extension products are employed in the subject methods to ultimately produce three different primer extension or PCR products. Each pair of oligonucleotide primers corresponds to a different potential reading frame of the three different possible reading frames of the DNA sequence of interest. As such, one set of oligonucleotide primers will generate a first type of PCR product corresponding to one of the three possible reading frames of the DNA sequence. Similarly, the second and third pairs of primers will generate PCR products corresponding to the remaining possible reading frames. In generating the PCR products with the set of three different pairs of primers, the vector may be contacted with the entire set of primers at substantially the same time, e.g. simultaneously, or the different pairs of primers may be contacted sequentially with the vector, such that each PCR product is generated at a different time.

The oligonucleotide primers of the set of three pairs of primers used in the subject methods will each comprise a first region of sequence identity with the vector (i.e. a region which makes them "universal" primers) and a second region that is capable of site specific recombination with the second vector, as described in greater detail below. The first region of sequence identity with the vector will be capable of annealing to the vector under appropriate conditions through base pairing hybridization, and therefore will be of sufficient length to provide for hybridization to complementary template DNA under annealing conditions, as described above, but will be of insufficient length to form stable hybrids with template DNA under polymerization conditions. The region of sequence identity in the primers will generally be at least 10 bp in length, usually at least 15 bp in length and more usually at least 16 bp in length and may be as long as 30 bp in length or longer, where the length of the first primer region will generally range from 15 to 30 bp in length, usually from about 20 to 25 bp in length.

Each of the oligonucleotide primers will also comprise a second region which does not hybridize under annealing conditions with the vector, but instead is permissive of, or capable of participating in, site specific (also known as homologous) recombination with the second vector. The second region may range in length from about 20 to 100 bp, and will usually range from about 30 to 80 bp, more usually from about 30 to 60 bp. In some embodiments according to the subject invention, at least one of the members of the primers in the set of three pairs of primers will comprise a second region that does not exceed about 50 bp, and usually does not exceed about 40 bp, and more usually does not exceed about 30 bp, and may be as short as 20 bp. Among primer pairs, the second region in each member of the pair may be substantially the same length or be of different lengths. The second region capable of site specific recombination may have the same length or a different length. For example, in one member of each pair of primers, the second region may be 60 to 80 bp in length, while the second region in the other member of the pair may be 20 to 50 bp in length. The first and second regions of the primers may be separated by a linking group, where the linking group may be of any convenient length.

Combination of the first vector with the set of primers into a reaction mixture under PCR conditions, as described above, results in the generation of three different PCR products, where the PCR products will be double stranded and each product will comprise the DNA sequence of interest flanked on either end with a region of sequence having sequence identity with the first vector and a region at each end of the product that is permissive of site specific recombination with the second vector. In other words, at the center of the primer extension product will be the DNA sequence of interest which is then flanked at both ends with a region of DNA having a sequence corresponding the flanking sequence of the DNA of interest in the first vector and then ending at both ends with a region of DNA that can recombine with the second vector through site specific recombination.

The next step of the subject methods comprises contacting the primer extension products with the second vector, e.g. an expression vector, under conditions sufficient for site specific recombination to occur such that the primer extension products are integrated into the second vector. The second vector will generally be a plasmid of about 2.5 to 15 kbp in length. The plasmid will typically comprise one or more selectable marker genes, such as LEU2, TRP1, HIS3, and the like, which enable the selection of successfully transformed hosts. In certain embodiments, the second vector will further comprise a gene or fragment thereof to which the DNA sequence of interest is to be joined in frame to enable expression of a fusion protein. For example, where the second vector is to be used as an expression vector in a two-hybrid assay, the plasmid may further comprise a fragment of a eukaryotic transcription activator, such as GAL4, an artificial activator such as B42, and the like, where the fragment encodes either the DNA binding domain or the activation domain of the transcription activator.

To provide for integration of PCR product comprising the DNA sequence of interest into the second vector, where the second vector is a plasmid, the plasmid will be linearized, conveniently with one or more restriction enzymes, to yield a linearized plasmid whose ends are capable of participating in site specific recombination with the PCR product with which they are combined. Typically, the circular plasmid will be treated with two different restriction enzymes to produce a linearized product so as to inhibit self-ligation of the linearized plasmid.

For site specific or homologous recombination, the PCR products and linear plasmids will generally be co-transformed into a suitable host, such as yeast, whereby recombination occurs. See Ma et al., Gene (1987) 58: 201–216; and Degryse et al., Yeast (1995) 11: 629–640, the disclosures of which are herein incorporated by reference. See also, Ishioka et al., infra.

Recombination of the PCR products with the linearized second vectors results in integration of the PCR products into the second vectors and concomitant transfer of the DNA sequence information of interest from the first vector to the second vector. The resultant recombinant vector comprising the DNA sequence information of interest can be recovered from the host using techniques known to those of skill in the art for subsequent use, as desired.

The subject methods find use in any application in which the transfer of sequence information from one vector to another is desired. Applications in which the subject methods find use include gene transfer from one vector to another, selection marker introduction or replacement, vector modification and mutagenesis of genes. The subject methods also find use in large scale cloning applications where DNA sequence information of a plurality of different first vectors is transferred into a plurality of different second vectors, where by plurality it meant at least 2, usually at least 5, more usually at least 10, and typically 50 or more, with no definitive upper limit. For example, the subject methods may be used to transfer a library of DNA fragments, where each fragment is present in a different first vector, e.g. a plasmid, such as a plasmid library of cDNA, genomic DNA, ESTs, and the like, from their initial first vectors to second vectors, such as yeast expression vectors. Such plasmid libraries of DNA fragments are known to those of skill in the art and may be purchased commercially from vendors such as Research Genetics, Clontech, Invitrogen, Stratagene and the like.

An example of a particular application in which the subject methods find use is what is known as the two-hybrid assay, such as two-hybrid assays based on the eukaryotic transcriptional activator GAL4. Briefly, in this assay a first expression vector is prepared that encodes a fusion protein of the GAL4 DNA binding domain and a first protein, i.e. the "bait" protein. A second expression vector is also prepared that encodes a fusion protein of the GAL4 activation domain and a protein suspected of binding to the target protein, i.e. the "prey." The prepared vectors are then co-transformed into a yeast host strain. If the bait binds to the target, the two GAL4 domains are brought together, which results in the production of a reporter signal. In this manner, the in vivo binding properties of previously uncharacterized proteins can be elucidated.

The subject methods can be used in such assays to rapidly and efficiently prepare a library of expression vectors for use in two-hybrid assay analysis, where each expression vector comprises a sequence of DNA encoding a different "bait" peptide, such as a different EST sequence. For example, from library of different ESTs present in plasmid vectors, the subject methods can be used to rapidly prepare a corresponding expression vector for each different EST for subsequent use in two-hybrid analysis to determine the binding characteristics of products encoded by the different EST sequences. Because universal primers are employed in the subject methods, the EST sequences need not be precharacterized. Furthermore, as site specific or homologous recombination is employed to introduce the EST sequence information into the expression vectors, the use of restriction enzymes and its concomitant complications can be avoided.

Also provided are kits for carrying out the subject methods. Kits according to the subject invention will at least comprise a set of three pairs of oligonucleotide primers, as described above. The kit may further comprise one or more second vectors, such as expression plasmids, where the expression plasmids may comprise a DNA fragment encoding a region of a eukaryotic transcriptional activator, such as GAL4, e.g. the GAL4 DNA binding domain or the GAL4 activation domain. The kits may also comprise additional reagents necessary for carrying out the subject methods, such as enzymes, buffers; the initial vector(s) comprising the DNA sequence of interest; and the like. The kits may further comprise additional components for use in a particular application. For example, also provided by the subject invention are kits for use in two-hybrid assays. Such kits comprise the components described above, such as the set of primers and expression vectors, and further comprise additional components employed in two-hybrid analysis, such as suitable yeast hosts, control vectors, reagents, growth media and the like. Such kits will also typically comprise user manuals or similar instructions, where such instructions may be associated with the labeling or packaging of the kit, or included as a package insert.

The following examples are offered by way of illustration and not by way of limitation.

EXPERIMENTAL

A. Yeast strain construction

A *Saccharomyces cerevisiae* strain YM4271 (MATa, ura3-52, his3-200, ade2-101, lys2-801, leu2-3, 112, trp1-903, tyr1-501, gal4-Δ512, gal80-Δ538, ade5::hisG) was from Clontech Laboratories, Inc (Palo Alto, Calif.). This strain was transformed with the plasmid DNA of p53BLUE (Clontech) linearized by restriction endonuclease Nco I, which cleaves p53BLUE within URA3 locus (Luo et al., "Cloning and Analysis of DNA-binding proteins by yeast one-hybrid and one-two-hybrid systems," *BioTechniques* (1996) 20, 564–568). The transformants were selected by plating on minimal medium SD lacking uracil. The resulting yeast (designated strain YL53B) contained three tandem copies of the consensus p53 binding sites upstream of reporter gene lacZ in the ura3 locus of its genome.

B. Polymerase chain reaction

Mouse p53 cDNA in pT7T3D-p53 was amplified by polymerase chain reaction (PCR) with the Advantage KlenTaq polymerase mix (Clontech). The sequences of PCR primers are composed of two portions: a 21-base fragment at their 3'-termini corresponding to the sequences in pT7T3D-p53 flanking the mouse p53 cDNA, and a fragment at their 5'-termini with different lengths (from 20 to 80 residues) corresponding to sequences of the multiple cloning sites of pACT2. The sequences of the longest forward (oligo 5'-80) and reverse (oligo 3'-80) primers are as follows:

5'-80: (SEQ ID NO:01)
5'-TATTCGATGATGAAGATACCCCACCAAACCCA-AAAAAAGAGATCTGTATGGCTTACCCATACAATG-TTCC AGATTACGCTGCTGGAGGCCCTCGAGGCC-AAGAATTC-3';

3'-80: (SEQ ID NO:02)
5'-GTATAAATGAAAGAAATTGAGATGGTGCACGA-TGCACAGTTGAAGTGAACTTGCGGGGTTT TTCAG-TATCTACGATTCACCCTCACTAAAGGGAATAAG-CTT-3'.

Other primers contained 20, 30, 40, 45, 50, 55 and 60 residues of homologous sequences, and were designated 5'-20, 5'-30, 5'-40, 5'-45, 5'-50, 5'-55, 5'-60, 3'-20, 3'-30, 3'-40, 3'-45, 3'-50, 3'-55 and 3'-60, respectively. The PCR amplification started with denaturation at 94° C. for 3 min., followed by 30 cycles of 15 sec. denaturation at 94° C. and 2 min. extension at 68° C. The resulting PCR products of p53 (around 2 kilo-base pairs in length) were confirmed on an agarose gel, and further purified with a PCR purification Kit (Qiagen) according to the manufacturer's instructions.

C. Yeast transformation

The plasmid DNA of pACT2, a yeast- *Escherichia coli* shuttle vector that contains a yeast LEU2 gene was digested overnight with Bam HI and Xho I, which are located in the multiple cloning site and thus linearized the vector at the downstream end of GAL4 activation domain. The digestion mix was extracted with phenol-chloroform, and the DNA was precipitated by ethanol. 500 ng of digested pACT2 and 500 ng of purified PCR products were mixed and cotransformed into yeast YL53B with the modified lithium acetate protocol (Ito et al., "Transformation of intact yeast cells treated with alkali cations," J. Bacteriol (1983)153: 163–168; Gietz, et al, "Improved method for high efficiency transformation of intact yeast cells," Nucleic Acids Res (1992)20: 1425) (YEASTMAKER transformation system, Clontech). One percent of the transformed yeast cells were plated on SD medium lacking leucine. Plasmid DNA in yeast was retrieved by using YEASTMAKER plasmid isolation kit (Clontech).

D. β-Galactosidase activity assay

Yeast colonies were lifted onto nylon membrane from a plate. The membrane was soaked in liquid nitrogen and thawed immediately at room temperature to permeabilize the cells. The β-galactosidase activity was detected by soaking the membrane with 100 mM phosphate buffer (pH 7.0), 1 mM $MgSO_4$, 10 mM KCl and 0.33 mg/ml X-gal (5-bromo-4-chloro-3-indolyl-β-D-galactopyranoside).

E. Results and Discussion

Mouse p53 cDNA was modified by using PCR approach. The p53 cDNA fragments were produced by using primers that contained 20, 30, 40, 45, 50, 60 or 80 nucleotide residues homologous to regions on pACT2 flanking the multiple cloning sites, which is located at the end of GAL4 activation domain, and 21 residues homologous to pT7T3D-p53 flanking the p53 cDNA. The PCR primers at the 5' end of p53 were designed in such a way that the amplified p53 cDNA would be able to generate an in-frame fusion protein with upstream GAL4 activation domain when it is integrated into pACT2 via homologous recombination. The amplified PCR products were cotransformed with Bam HI/Xho I-linearized pACT2 into *S. cerevisiae* YL53B that contains three tandem copies of the consensus p53 binding sites upstream of the reporter gene lacZ (see above). pACT2 containing-yeast cells were selected on SD/-Leu plates and GAL4-p53 fusion protein expression colonies resulted from in vivo homologous recombination were screened by filter-lift β-galactosidase activity assay.

The results in Table 1 show that a higher yield of transformants was achieved when the length of homologous region was increased. The results show that homologous recombination in yeast can occur when as short as 20 bp of homology on each side is present between the linearized vector and its homologous fragment. We observed 3.4% of the transformants expressing β-galactosidase. The percentage of transformants expressing GAL4-p53 fusion protein jumped to 78.9% with 30 bp of homology on each side, and to 93.3% with 40 bp of homology. Furthermore, when more than 60 bp of homologous sequence is present at each end, the percentage of lacZ positive colonies reached higher than 95% and the total number of transformants was over 2×10⁵ per microgram of total DNA (at the molar ratio of approximately 1:4 for vector:fragment). The above results were confirmed by sequence analysis, in which recombinant plasmid derived from p53 cDNA fragment with 60 bp of homologous sequence were isolated from four randomly picked yeast colonies. Sequence determination of the recombination regions showed that all contained anticipated sequences.

We also analyzed the effect on recombination of asymmetrical length of homology at both sides. We amplified p53 at one end with 80 bp homology and the other with 20, 30, 40, 45 or 50 bp in length. The results in Table 1 indicate that when the p53 fragment contained 20 bp of homology at one side and 80 bp at the other, over 45.6% of the transformants were derived from homologous recombination. The recombination frequency increased to over 93% when one side had more than 30 bp in homology. Comparison of these results with those of equal length on both ends suggests that one end with a long homologous sequence can significantly facilitate the other end with short homologous sequence in the recombination process. On the other hand, there was essentially no difference observed when this 80 bp of homology was located at the 5' side or at the 3' side of p53, suggesting that there is no specific sequence preference for the homologous recombination. In our experiments, we linearized the vector with two restriction enzymes (Bam HI and Xho I) at the multiple cloning sites to prevent self-ligation in yeast (Glasunov, et al., "Different repair kinetics for short and long DNA double-strand gaps in *Saccharomyces cerevisiae,*" Int. J. Radat. Biol (1995)68: 412–428). However, we still observed that certain percentage of transformants (approximately 2–4% of the colonies when each end contained more than 60 bp of homologous sequences) were lacZ-negative, presumably due to incomplete digestion and/ or mutations introduced into p53 by PCR (Ishioka, et al., "Screening patients for heterozygous p53 mutations using a functional assay in yeast," Nature Genet (1993)5: 124–129). On the other hand, treatment of linearized vector with calf intestine phosphatase showed no improved efficiency in the current experiments. We also observed that same amount of PCR products before or after purification were equally effective in the homologous recombination.

TABLE 1

Table 1. Results of in vivo cloning by homologous recombination in yeast. Mouse p53 cDNA with different lengths of homologous sequence at each end was transformed into *S. cerevisiae* YL53B with linearized vector pACT2. The transformants were selected on SD/–Leu. Total number of colonies was counted. Colonies expressing lacZ gene were detected by colony-lifting β-galactosidase activity assay.

| Homology length (bp) colonies | Total colony # | % lacZ positive |
|---|---|---|
| 0-0[a] | 72 ± 8.4[b] | 0 ± 0.0 |
| 20-20 | 88 ± 10.6 | 3.4 ± 0.4 |
| 30-30 | 815 ± 106.1 | 78.9 ± 9.8 |

TABLE 1-continued

Table 1. Results of in vivo cloning by homologous recombination in yeast. Mouse p53 cDNA with different lengths of homologous sequence at each end was transformed into *S. cerevisiae* YL53B with linearized vector pACT2. The transformants were selected on SD/–Leu. Total number of colonies was counted. Colonies expressing lacZ gene were detected by colony-lifting β-galactosidase activity assay.

| Homology length (bp) colonies | Total colony # | % lacZ positive |
|---|---|---|
| 40-40 | 926 ± 14.2 | 93.3 ± 1.9 |
| 45-45 | 1084 ± 15.6 | 93.6 ± 1.6 |
| 50-50 | 1120 ± 54.4 | 93.8 ± 1.2 |
| 60-60 | 2234 ± 314.5 | 95.8 ± 2.3 |
| 80-80 | 2308 ± 121.6 | 98.1 ± 1.2 |
| 20-80 | 325 ± 36.1 | 45.6 ± 3.4 |
| 30-80 | 1261 ± 176.1 | 94.2 ± 2.4 |
| 40-80 | 1445 ± 162.3 | 95.7 ± 2.3 |
| 45-80 | 1465 ± 77.8 | 95.2 ± 1.2 |
| 50-80 | 1632 ± 116.6 | 97.2 ± 1.9 |
| 80-20 | 292 ± 5.9 | 46.2 ± 0.5 |
| 80-30 | 1184 ± 121.6 | 93.5 ± 1.1 |
| 80-40 | 1457 ± 243.6 | 94.4 ± 2.4 |
| 80-45 | 1670 ± 84.2 | 95.7 ± 1.3 |
| 80-50 | 1865 ± 120.0 | 96.6 ± 1.6 |

[a]Length of homologous regions at both ends of the PCR-amplified p53, e.g. 20-80 means 20 bp at its upstream end and 80 bp at its downstream end.
[b]Average ± s.d. based on two experiments.

It is evident from the above discussion and results that new methods of transferring DNA sequence information from a first vector to second vector are provided. Because the subject methods use universal primers that have sequence identity with the first vector flanking the DNA sequence of interest, the DNA sequence of interest need not be known. Because the subject methods of transferring DNA sequence information require relatively few steps, they are more efficient and less expensive to perform than other methods of DNA transfer between vectors, and therefore particularly applicable to large scale applications in which a large number of DNA fragments of unknown sequence present in plasmid vectors are transferred to second vectors, such as expression vectors.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of transferring DNA sequence information from a first vector to a second vector, said method comprising:
   contacting said first vector with a set of three pairs of oligonucleotide primers under conditions sufficient to produce three different PCR products, wherein each oligonucleotide primer comprises a first region of sequence identity with said first vector and a second region which does not hybridize with said first vector and provides for homologous recombination with said second vector, whereby three different PCR products are produced; and
   contacting said three different PCR products with said second vector under conditions sufficient for homologous recombination to occur;
   whereby said DNA sequence information is transferred from said first vector to said second vector.

2. The method according to claim 1, wherein said DNA sequence information is the sequence of an EST clone.

3. The method according to claim 1, wherein said three different PCR products correspond to three different reading frames.

4. The method according to claim 1, wherein each pair of said set of oligonucleotide primers is contacted with said first vector at substantially the same time.

5. The method according to claim 1, wherein each pair of said set of oligonucleotide primers is contacted with said first vector at different times.

6. A second vector produced according to claim 1, wherein each of the first regions in said set of primers is the same length.

7. A method of transferring DNA sequence information from a first plasmid to a second plasmid, said method comprising:
   contacting a first plasmid with a set of three pairs of oligonucleotide primers under conditions sufficient to produce three different PCR products, wherein each PCR product corresponds to a different reading frame and each oligonucleotide primer comprises a first region of sequence identity with said first plasmid and a second region which does not hybridize with said first plasmid and provides for homologous recombination with said second plasmid, whereby three different PCR products are produced; and
   contacting said three different PCR products, with said second plasmid under conditions sufficient for homologous recombination to occur;
   whereby said DNA information is transferred from said first plasmid to said second plasmid.

8. The method according to claim 7, wherein each pair of said set of oligonucleotide primers is contacted with said first plasmid at substantially the same time.

9. The method according to claim 7, wherein each pair of said set of oligonucleotide primers is contacted with said first plasmid at different times.

10. The method according to claim 7, wherein said second plasmid is a DNA sequence encoding either a DNA binding domain or an activation domain of a eukaryotic transcriptional activator.

11. A second plasmid produced according to claim 7, wherein each of the first regions in said set of primers is the same length.

12. A method of transferring DNA sequence information from a first plasmid into an expression plasmid, said method comprising:
   contacting said first plasmid with a set of three pairs of oligonucleotide primers under conditions sufficient to produce three different PCR products, wherein each PCR product corresponds to a different reading frame and each oligonucleotide primer comprises a first region of sequence identity with said first plasmid and a second region which does not hybridize with said first plasmid and provides for homologous recombination with said expression plasmid, whereby three different PCR products are produced; and
   co-transforming said three different PCR products and said expression plasmid into a yeast host whereby homologous recombination occurs, wherein said expression plasmid comprises a DNA sequence encoding either a DNA binding domain or an activation domain of a eukaryotic transcriptional activator;
   whereby said DNA sequence information is transferred into said expression plasmid.

13. The method according to claim 12, wherein each pair of said set of oligonucleotide primers is contacted with said first plasmid at substantially the same time.

14. The method according to claim 12, wherein each pair of said set of oligonucleotide primers is contacted with said first plasmid at different times.

15. The method according to claim 12, wherein said eukaryotic transcriptional activator is GAL4.

16. The method according to claim 12, wherein said second region ranges in length from 20 to 80 bp.

17. An expression plasmid produced according to claim 12, wherein each of the first regions in said set of primers is the same length.

18. The method according to claim 16, wherein said second region does not exceed 50 bp in length.

19. A kit for use in transferring DNA sequence information from a first vector to a second vector, said kit comprising:
- a set of three pairs of oligonucleotide primers, wherein each primer comprises a first region of sequence identity with said first vector and a second region which does not hybridize with said first vector and provides for homologous recombination with said second vector.

20. The kit according to claim 19, wherein said second vector is an expression plasmid comprising a sequence encoding either a DNA binding domain or an activation domain of a eukaryotic transcriptional activator.

21. The kit according to claim 20, wherein said kit further comprises two different expression plasmids, wherein each plasmid comprises said sequence encoding either said DNA binding domain or said activation domain.

22. A kit for use in transferring DNA sequence information from a first plasmid to an expression plasmid, said kit comprising:
- an expression plasmid comprising a sequence encoding either a GAL4 DNA binding domain or a GAL4 activation domain;
- a set of three pairs of oligonucleotide primers, wherein each primer comprises a first region of sequence identity with a first plasmid and a second region which does not hybridize with said first plasmid and provides for homologous recombination with said expression plasmid.

* * * * *

SEQUENCE LISTING

<160> NUMBER OF SEQ ID NOS: 2

<210> SEQ ID NO 1
<211> LENGTH: 107

```
-continued

<212> TYPE: DNA
<213> ORGANISM: Artificial Sequence
<220> FEATURE:
<223> OTHER INFORMATION: PCR primer

<400> SEQUENCE: 1
tattcgatga tgaagatacc ccaccaaacc caaaaaaaga gatctgtatg gcttacccat      60
acaatgttcc agattacgct gctggaggcc ctcgaggcca agaattc                  107

<210> SEQ ID NO 2
<211> LENGTH: 102
<212> TYPE: DNA
<213> ORGANISM: Artificial Sequence
<220> FEATURE:
<223> OTHER INFORMATION: PCR primer

<400> SEQUENCE: 2
gtataaatga aagaaattga gatggtgcac gatgcacagt tgaagtgaac ttgcggggtt     60
tttcagtatc tacgattcac cctcactaaa gggaataagc tt                       102
```